United States Patent [19]

Gores

[11] 4,396,375
[45] Aug. 2, 1983

[54] DENTAL PACKING TOOL FOR GINGIVAL RETRACTION CORD

[76] Inventor: Kenneth W. Gores, c/o Bellevue Medical Dental Center, 1026 - 112th St., NE., Bellevue, Wash. 98004

[21] Appl. No.: 369,161

[22] Filed: Apr. 16, 1982

[51] Int. Cl.³ .............................................. A61C 3/00
[52] U.S. Cl. .................................................. 433/141
[58] Field of Search ......................................... 433/141

[56] References Cited
U.S. PATENT DOCUMENTS 3,721,006  3/1973  Malmin ................................ 433/141

Primary Examiner—Robert Peshock
Attorney, Agent, or Firm—Ford E. Smith; David L. Garrison

[57] ABSTRACT

This instrument is a dental hand piece having an angularly disposed working end provided with an easily rotated broad-faced but thin tamping or packing tool for forcing packing material such as cord or yarn strands into the sulcus or gingival crevice between a tooth and the crest of the gingival or gum tissue surrounding the tooth.

5 Claims, 6 Drawing Figures

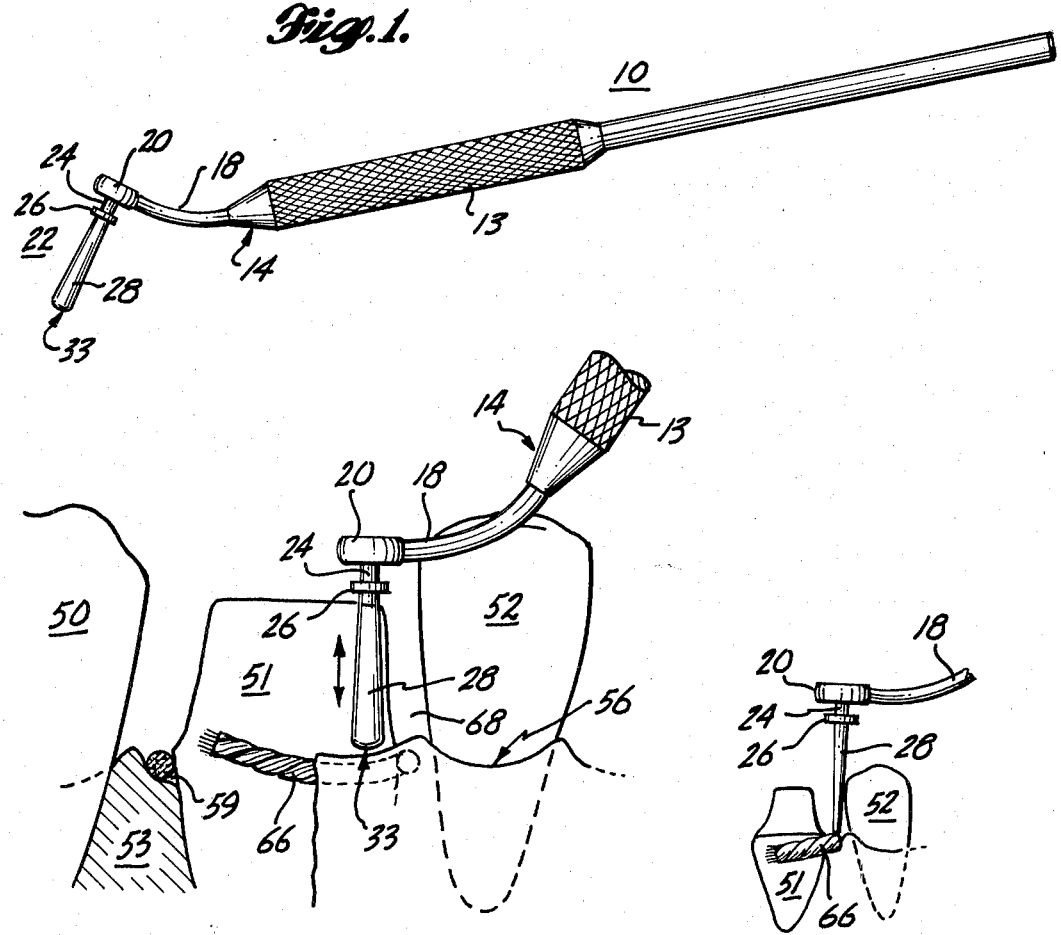

DENTAL PACKING TOOL FOR GINGIVAL RETRACTION CORD

SUMMARY OF THE INVENTION

So far as applicant knows, the only instruments available for the placement of retraction cord material into gingival crevices have fixed non-rotatable working ends that are incapable of automatically following the contours of the sulcus around a tooth at the gumline. Such fixed-end tools are usually double-ended and shaped so that opposite ends have differently angled tips. The dentist uses one or the other angle in his attempts to follow the sulcus in its, generally, circular path around the neck of a tooth. Much finger and hand dexterity is required. At best the operation is time consuming, awkward and immeasurably extends the patient's discomfort. These prior instruments not only tediously prolong the time of practice of the tooth-packing technique but they also introduce the possibility of improper or incomplete packing to the detriment of accuracy of the subsequent modeling and casting operations. It has been observed that with the prior tools, in packing materials into either the facial-lingual or mesial-distal crevices the dentist usually reverses the tool end-for-end about 20 times, possibly more. The work is tedious, requires excessive finger dexterity and skill, not always with completely satisfactory results.

DESCRIPTION OF THE DRAWINGS

FIG. 1 is a view in side elevation of a dental packing instrument embodying the invention herein;

FIG. 2 is an enlarged view of a portion of the tool and demonstrating the field of use;

FIG. 3 is another schematic view, partially in cross-section, showing the tool in use to pack in the intertooth spaces;

FIG. 4 is an enlarged view of the working member of the instrument showing its mounting in a frictionless bearing;

FIG. 5 is a cross-section on line 5—5 of FIG. 4; and

FIG. 6 is a diagrammatic view illustrating the gingiva and its parts.

DETAILED DESCRIPTION OF THE INVENTION

In dentistry it often becomes necessary to take an impression of one or all of the teeth of a person's jaw. Usually such an impression is made from material that molds easily, firmly quickly and produces a highly accurate mold for the subsequent production of an exact replica of the molded portions of a patient's jaw. It is common practice to pack (between the margins and the usually contiguous gum tissue) a cord, string or yan strand which separates and holds the gum tissue spaced away at the sulcus from the teeth below the gumline.

Referring to FIGS. 2 and 3, there will be seen several teeth 50, 51 and 52 supported in side-by-side relation in the alveolar parts (not shown) of a human jaw. The fleshy tissue 53 covers the alveolar parts and also fully envelopes the necks of the teeth 50.

In the interest of understanding the field of use of the invention herein, refer to FIG. 6. The tooth 51 is shown prepared for receiving a crown. The dotted line 54 represents the tooth before preparation and indicates the portions removed in the shaping of the truncated pyramidal portion 55. The tissue 53 rises to the gingival crests 56, 57 and then descends adjacent the tooth to form the gingival crevice or sulcus 58 and 59.

The invention herein is useful for and is employed in packing a flexible strand or string 66 between and around the teeth 50–51 and 51–52 and into the crevices and the enveloping fleshy tissue 53 beneath or inside of the patient's gums. Usually the packing material is moistened or contains medicinal material. Normally it is soft and harmless to tissue. A jaw or a portion thereof thus packed permits a dentist or assistant to make an impression not only of the teeth above or below the fleshy tissue but also a short distance within the enveloping tissue at the gumlines. Thus more of the tooth, including particularly the subgingival margins of the tooth, is exposed and will be reproduced in the model eventually made from the impression.

The dental instrument of FIG. 1 comprises a handle 10 shank having a cylindrical gripping portion 13, which may be knurled for ease of manipulation. The tool is held very much as one grips a pencil or pen. The tapered working end 14 receives shank 18, the outer end of which includes working head 20 of the packer.

Packer member 22 comprises stem 24 above collar 26 and includes the working blade 28 having opposed, broad faces 30 and relatively thinner edges 32. The blade 28 at its sides tapers and converges to form the working end 33 which is used to tamp or press the gingival retraction cord 56 inward at the gumline into the crevices alongside a tooth and between it and the surrounding tissue 53, thus exposing the subgingival margins.

The design shown in FIG. 4 includes a permanently lubricated, frictionless ball-bearing 38 seated in a socket within head 20. Antifriction bearing 38 removably receives, journals and rotatably supports shank or pin 34 of the packer tool 22. Packing tools of various shapes, styled for different functions, may be supplied for quick change or replacement. The interchangeable blades of various tools may be longer and thinner for working abound anterior teeth, and shorter and broader for packing around posterior teeth. The plain tips shown, of course, may be slightly serrated to facilitate retracting end packing in hard to reach locations.

In use the instrument 10, is held by a dentist somewhat as one holds a pencil. The working head 20 and packer tool 22 are introduced to the mouth. A broad face 30 of blade 28 is caused to bear on a face of a tooth. If perchance an edge 32 of the tamping blade makes the initial contact in a perpendicular manner to the tooth, the tool will automatically and immediately rotate to bring about broad face contact. In other words, there is practical self-aligning of the tamping end 33 of the blade with the adjacent face of the tooth throughout the entire closed, curved path it must follow to pack the entire gingival crevice. In any disposition, the tool's working end 33 may be used to press on strand or string 66 to ease it with at the most nominal discomfort for the patient at the gumline 54 into the gingival crevice or sulcus 58 between the tooth and the surrounding tissue 53, thereby to separate and distend the gingival crest tissue 57 from the tooth.

As the dentist works his way along the gingival crevice around a tooth, the tool automatically rotates as its inner face bears on and follows the tooth contours and thus maintains substantial parallelism with the tooth surfaces. As the worker approaches the interspace 68, as in FIG. 2, the tool handle may be tilted and adjusted as to its attack angle so that the working tip enters space 58 and the string or cord is forced into place. A skillful person may efficiently make the full closed circuit of a tooth without ever removing the tool from the crevice.

Free frictionless rotation of tool 22 is the practical secret of the success of the tool and makes very simple the technique to which it relates. The shank 24 may be easily withdrawn from bearing 38 as packing tools of different shapes are substituted with ease.

It will, of course, occur to those skilled in the art that variations and alterations of size, shape or function may be desirable. All such as are fairly encompassed by the following claims, having due regard to an appropriate application of the doctrine of equivalents, are intended to be covered by this patent.

What is claimed is:

1. A packing tool for dentists' use in packing a flexible cord or the like about a person's tooth below the gumline in the subgingival crevices, comprising:
   a manually manipulable rigid handpiece;
   a blunt end packing blade having greater width than thickness and including a longitudinally extending stem; and
   in association with said packing blade stem at an end of said handpiece, means for receiving and retaining said stem for free rotation of said blade about the axis of said shank as the same is moved in a progressively advancing, tamping motion at a person's gumline, with a broad surface of the blade in close juxtaposition to a tooth in such person's mouth.

2. The invention of claim 1, in which the blade stem is removably received in a socket carried by said handpiece.

3. The invention of claim 1, in which the blade shank is seated in an anti-friction means adapted to rotatably retain the shank against longitudinal dislocation.

4. The invention of claim 1, in which the blade shank is nonremovable journaled in said receiving means at an end of said handpiece.

5. A packing tool for dentists' use in packing a flexible cord or the like about a person's tooth below the gumline comprising:
   a manually manipulable rigid handpiece having an angularly disposed shank at its working end provided with a friction-free socket;
   a double-ended pin having one end journaled in said socket and its other end extending in line therewith;
   a blunt-end packing blade having greater width than thickness and including a longitudinally aligned stem;
   said socket being adapted for receiving and retaining said stem for rotation of said blade about the axis of said socket as the same is moved in a progressively advancing, tamping motion at a person's gumlin, with a broad surface of the blade in close juxtaposition to a tooth in a person's mouth.

* * * * *